(12) United States Patent
Wang et al.

(10) Patent No.: US 6,375,826 B1
(45) Date of Patent: Apr. 23, 2002

(54) ELECTRO-POLISHING FIXTURE AND ELECTROLYTE SOLUTION FOR POLISHING STENTS AND METHOD

(75) Inventors: Jingli Wang, Berkeley; Christopher J. Tarapata, Santa Clara; Matthew J. Fitz, Sunnyvale, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/503,280

(22) Filed: Feb. 14, 2000

(51) Int. Cl.[7] .............................. C25F 3/16; C25F 7/00
(52) U.S. Cl. ................. 205/684; 205/686; 204/224 M; 204/272
(58) Field of Search .............................. 205/640, 684, 205/686; 204/224 M, 272

(56) References Cited

U.S. PATENT DOCUMENTS 5,507,923 A * 4/1996 Stouse et al. .......... 204/224 M
5,997,703 A * 12/1999 Richter .................. 204/224 M

FOREIGN PATENT DOCUMENTS

| WO | WO 98/51238 | 11/1998 |
| WO | WO 2001/06954 | 1/2001 |

* cited by examiner

*Primary Examiner*—Donald R. Valentine
(74) *Attorney, Agent, or Firm*—Fulwider Patton Lee & Utecht, LLP

(57) ABSTRACT

An electro-polishing fixture for polishing stents which incorporates multiple anodes in contact with the stent and a center cathode disposed coaxially within the interior of the stent and a curved exterior cathode disposed about the perimeter of the stent. The invention further includes an electrolyte solution adapted for polishing stents composed of nickel-titanium alloy and a method of using the electrolyte in combination with the electro-polishing fixture.

20 Claims, 2 Drawing Sheets

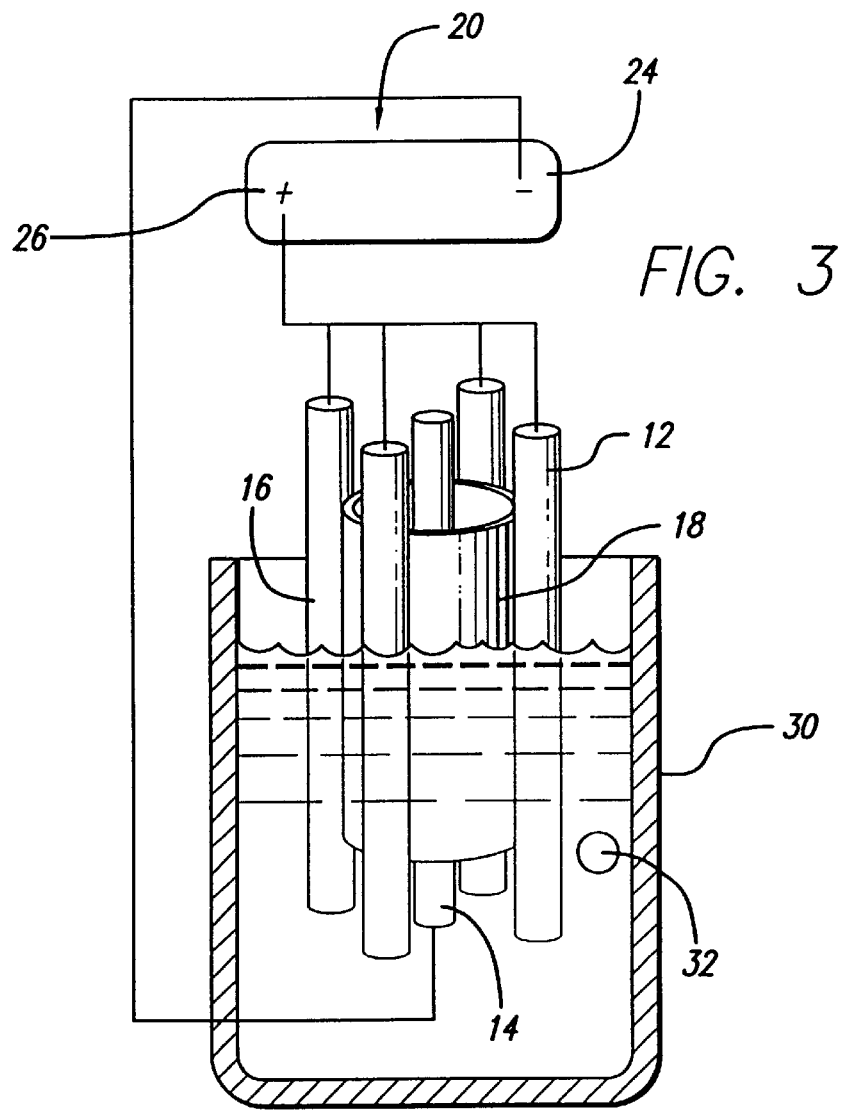
FIG. 3
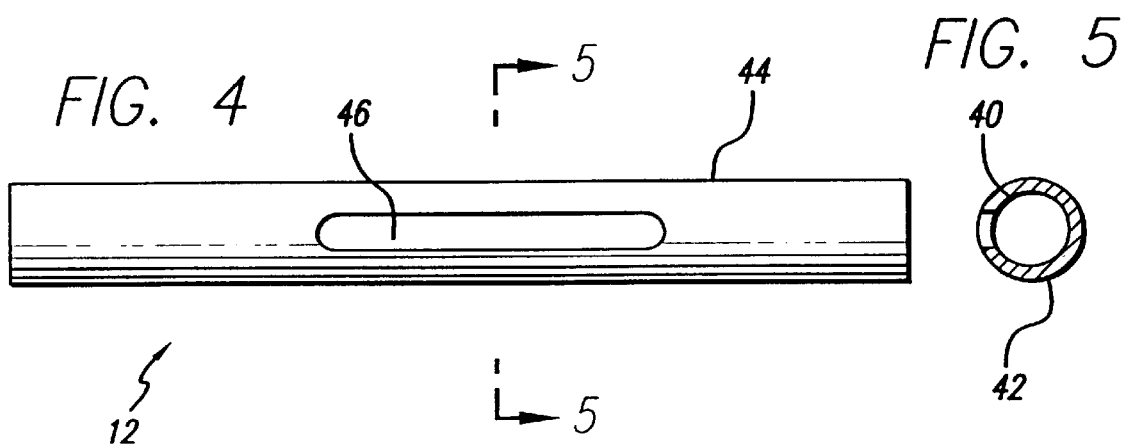
FIG. 4
FIG. 5

ELECTRO-POLISHING FIXTURE AND ELECTROLYTE SOLUTION FOR POLISHING STENTS AND METHOD

BACKGROUND OF THE INVENTION

The present invention is directed to the field of electro-polishing metallic stents, with particular application to stents manufactured from nickel-titanium and stainless steel alloys.

Stents are used in conjunction with a medical procedure known as balloon angioplasty which is used to restore blood flow through obstructed or partially obstructed arteries. In an angioplasty procedure, a balloon catheter is inserted into an artery and advanced to the site of an arterial lesion. Subsequently, the catheter balloon is inflated to expand the artery and compress the accumulated atherosclerotic plaque which forms the arterial lesion against the artery wall, thereby restoring blood flow through the vessel. In a certain percentage of cases, the expanded artery will collapse after deflation of the catheter balloon or will slowly narrow over a period of time. To solve this problem, intravascular prostheses commonly referred to as stents have been developed.

A stent generally consists of a small, expandable, tubular metallic structure. There are two broad categories of stents in common use, self-expanding stents and balloon expandable stents. One type of self-expanding stent is a tubular member made from a nickel-titanium alloy. Alloys of this type possess what is commonly referred to as shape memory ability. Upon absorption of heat, these alloys will expand while undergoing a phase transformation from martensite to austenite. In nickel-titanium alloys used for stent applications, this phase change occurs at a temperature below the mean human body temperature of 98.6 degrees Fahrenheit. Typically, a nickel-titanium alloy stent is delivered to lesion site by means of a catheter designed to receive and chill the stent. Upon delivery to a lesion site, the stent expands radially to contact the artery walls upon being warmed to body temperature.

A balloon expandable stent by contrast is typically made from a deformable metallic material and is crimped onto the balloon portion of a balloon delivery catheter. Upon delivery to a lesion site, the stent is expanded radially, by inflating the catheter balloon, until it contacts the walls of an artery. With either type of stent, the expanded stent is left in place after withdrawal of the delivery catheter. The expanded stent supports the interior wall of the blood vessel and thereby prevents the blood vessel from collapsing or narrowing over time.

Stents are commonly manufactured from stainless steel, nickel-titanium alloys, and other materials. Stents are typically formed by machining selected patterns into drawn tubes of the desired material. The machining processes typically used are either Electro-Discharge Machining ("EDM"), which is based on the principle of erosion of metals by spark discharges, or Laser Beam Machining ("LBM"), which uses a narrow beam of light of high energy density to vaporize selected portions of the drawn metallic tube. Either machining process leaves a thin heat effected zone around the pattern cut in the drawn tube and a resulting surface finish that is coarse and unsuitable for implantation in living tissue. The surface finish of stents in the "as machined" condition is on the order of about 50–100 microns, while stents suitable for implantation within a blood vessel require a surface finish of about 0.2 to 0.05 microns. A surface roughness of 0.2 microns corresponds to a fine buff finish, while a surface roughness of 0.05 microns corresponds to a mirror-like polish.

To achieve the required surface finish, stents are typically descaled and electro-polished. After polishing, the stents are typically passivated to protect the polished surface. One method of descaling involves immersing the stents in an alkaline cleaner and ultrasonically agitating the stents for a selected period of time. Another method involves bead blasting stents with fine glass beads. There are other procedures for descaling which are well known to those skilled in the art.

The principles of electro-polishing, particularly with regard to stainless steel alloys, are also known in the art. Typically, an item to be electro-polished is immersed in an electrolyte which comprises an aqueous acidic solution. The item to be polished is made a positive electrode (anode) and a negative electrode (cathode) is placed in close proximity to the anode. The anode and cathode are connected to a source of electric potential difference with the electrolyte completing the circuit between anode and cathode. Upon the passage of electric current through the electrolyte, metal is dissolved from the anode surface with protrusions being dissolved faster than depressions, thereby producing a smooth surface. The rate of material removal in an electro-polishing process is primarily a function of the electrolyte chosen and the current density in the electrolyte fluid.

Typically, with stainless steel stents, a final step in the electro-polishing process involves passivation of the newly polished surface. After removal from the electrolyte solution and rinsing with water, residual anions of the acid used in the electrolyte remain in contact with the polished surface. The presence of such surface anions leads to deterioration of the newly polished surface when the residual anions come into contact with calcium and magnesium ions which are commonly found in non-deionized water (ordinary tap water). To prevent surface deterioration, newly polished stents are immersed in a passivation bath which typically consists of a solution of nitric acid, deionized water, and sodium dichromate. The passivation bath neutralizes the residual anions and leaves a protective, corrosion resistant, strongly adherent, transparent, chromium dioxide coating on the newly polished surface.

With nickel-titanium alloy stents, however, the passivation step is generally not required. Nickel-titanium alloys tend to form a titanium oxide rich surface layer during initial heat treatment of the alloy which renders the alloy relatively impervious to the corrosive effects of any residual anions that may be left on the stent surface after electro-polishing.

Although electro-polishing has proven to be an effective method of obtaining extremely smooth surfaces on the order of 0.2 to 0.05 microns surface roughness on relatively flat surfaces, simple immersion in an electrolytic bath has proven ineffective in obtaining a uniform degree of polish on both the interior and exterior surfaces of a tubular stent. What is needed to solve this problem is a stent polishing fixture that is able to maintain a uniform current density in the electrolyte solution within the interior of a stent as well as a uniform current density in the electrolyte solution about the exterior of a stent. In addition, electrolyte solutions specifically formulated for use with nickel-titanium alloys are needed as typical solutions formulated for use with stainless steel, generally have not been able to achieve the desired surface finish. The present invention satisfies these and other needs.

SUMMARY OF THE INVENTION

The present invention provides an electro-polishing fixture for providing a fine uniform polish on both the interior and exterior surfaces of metallic stents. The fixture achieves this result by providing a plurality of anodes around the circumference of a stent thereby creating uniform current density in the surrounding electrolyte when the stent is place within an electrolytic bath. The fixture of the present invention further includes a center cathode centrally located within the interior of a stent, which provides for uniform polishing of a stent's interior surface. The invention also includes a curved exterior cathode disposed about the perimeter of the stent which provides for uniform polishing of a stent's exterior surface. The combination of dual interior and exterior cathodes in conjunction with a plurality of anodes provides a high degree of uniformity in polishing.

The present invention further includes an electrolyte solution which is particularly well suited for producing a fine polish on stents made from nickel-titanium alloys and a method of using the electro-polishing fixture and the electrolyte of the present invention to polish nickel-titanium alloy stents. Other features and advantages of the present invention will become apparent from the following detailed description.

BRIEF DESCRIPTION OF THE DRAWINGS

FIG. 3 is a side view of the electro-polishing fixture of FIG. 1, shown in an electrolytic bath;

FIG. 4 is a side view of an anode which forms part of the electro-polishing fixture shown in FIG. 1.

FIG. 5 is cross sectional view, taken along the line 5—5, of the anode shown in FIG. 4.

DETAILED DESCRIPTION OF THE PREFERRED EMBODIMENT

Figure 1:
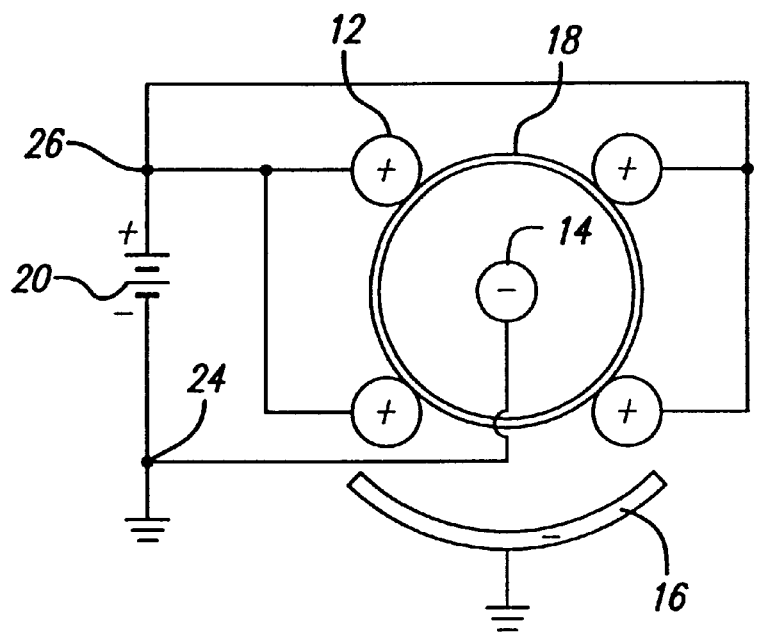
FIG. 1 is a top view of an electro-polishing fixture according to the present invention.
Figure 2:
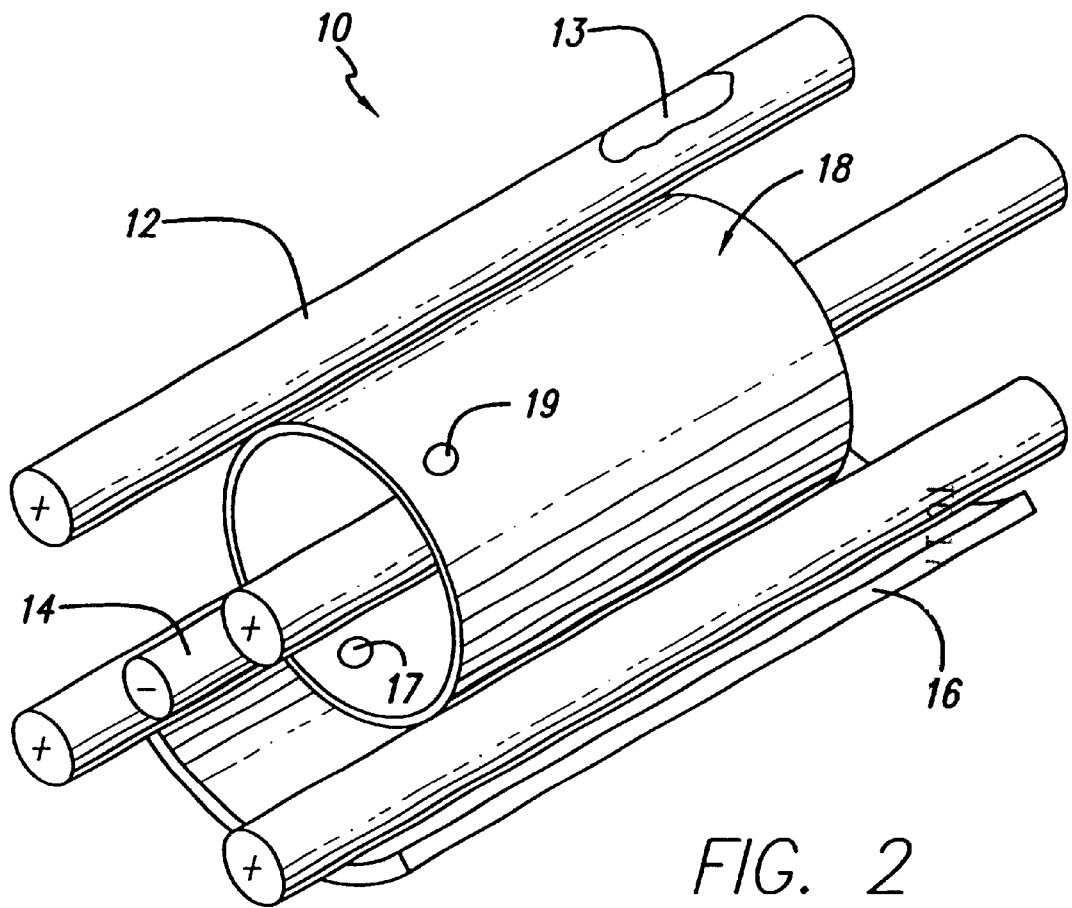
FIG. 2 is a perspective view of the electro-polishing fixture shown in FIG. 1, depicting the spatial relationships of the components of the fixture with regard to a stent to be polished.

Referring now to FIGS. 1–2, a stent polishing fixture 10 of the present invention is depicted which includes a plurality of holding anodes 12, an interior center cathode 14, and an exterior curved cathode 16. The stent polishing fixture 10 also includes a frame (not shown) for positioning the anodes 12, the center cathode 14, and the curved cathode 16, in a fixed spatial relationship with respect to a tubular stent 18 to be polished. The stent 18 to be polished, is shown schematically in the drawings and includes a cylindrical interior surface 17 and a cylindrical exterior surface 19. By utilizing the center cathode 14 within the interior of the stent and the curved exterior cathode 16 about the perimeter of the stent, uniform polishing of both the inside and outside surfaces 17 and 19 of the stent can be achieved simultaneously. Uniform polishing of the interior and exterior surfaces of the stent is further enhanced by equally spacing the anodes 12 around the perimeter of the stent, thereby maintaining a uniform electric field density between the stent and the center cathode 14 and the exterior cathode 16.

Referring now to FIG. 4, each anode 12 includes a core wire 40 made from a nickel-titanium alloy. Other metals such as platinum and platinum-iridium alloys are also suitable. To minimize electro-polishing of the anodes 12, each core wire 40 is sheathed by a layer 42 of inert polytetrafluoroethylene (PTFE) or fluorinated ethylenepropylene copolymer (FEP) material. TEFLON is a suitable material. A slot 44 is cut through the inert layer 42 which exposes a section of bare nickel-titanium wire 46. The length of the slot 44 corresponds to the length of the stent to be polished. The bare section of nickel-titanium wire 46 defined by the slot 44 is in continuous metal-to-metal contact with the stent 18 to be polished.

To achieve uniform polishing, the electrolyte solution should have a resistivity 200–300 times greater than that of the stent to be polished. The higher resistivity is required to maintain a preferred current path through the stent. If the resistivity of the electrolyte solution is too low, a non-uniform electrical field density may result between the stent 18 and the cathodes 14 and 16, leading to non-uniform polishing of the stent. By contrast, if the resistivity of the electrolyte solution is too high, the anodes 12 may tend to melt in the solution.

The center cathode 14 is formed as a straight cylindrical rod. The curved cathode 16 may be formed from wire mesh, sheet, or plate stock. The center cathode 14 and the curved cathode 16 are made from platinum. As will be appreciated by those skilled in the art, other materials such as nickel-titanium and platinum-iridium alloys are also suitable. The curved cathode 16 is formed as a cylindrical sector and is concentric with the stent 18. The curved cathode 16 also includes a longitudinal axis of symmetry which is substantially parallel to the longitudinal axis of the stent 18.

The preferred embodiments of the curved cathode 16 include cathodes with arc lengths of 180 degrees and 360 degrees. A 360 degree cathode is able to achieve an acceptable degree of polish with a minimum polishing time. However, a finer degree of polish may be achieved with the 180 degree cathode at the expense of a longer polishing time. Although the preferred embodiments of curved cathode 16 have been described as possessing arc lengths of 180 and 360 degrees, this is not meant to limiting. The curved cathode 16 may be made with an arc length substantially smaller than 180 degrees and in some circumstances, where an extremely fine degree of polish on a stent is required, a smaller arc length for the curved cathode 16 may be preferred.

Generally, the anodes 12 and the cathodes 14 and 16 are longer than the stent to be polished. In the preferred embodiment, the stent to be polished is centered approximately at the midpoint of the anodes and cathodes. The specific dimensions of the holding anodes 12, the center cathode 14, and the exterior curved cathode 16, are determined by the dimensions of the stent to be polished.

The frame for the holding anodes 12, the center cathode 14, the curved cathode 16, and the stent 18, may be of any suitable configuration that supports the anodes and cathodes in the desired fixed spaced relationship. The anodes 12 should be arranged so that they are parallel to each other and parallel to the longitudinal axis of the stent 18. The anodes 12 are preferably equally spaced around the perimeter of the stent 18. Each anode 12 is in physical and electrical contact with the stent 18 along the length of the stent. The center cathode 14 should be positioned so that it extends through the interior of stent 18 and is substantially coincident with the longitudinal axis of the stent 18. The curved cathode 16 should be positioned so that it is concentric with the stent 18 and is disposed at a selected radial distance from the exterior of the stent. Preferably, the frame should additionally provide electrical connections between the anodes, cathodes and a source of electric potential difference and a means for rotating the stent 18 within the support anodes 12. The frame may be made of any non-conductive, electrolyte resistant material. Polytetrafluoroethylene (PTFE) is a suitable material for construction of the frame.

FIGS. 2 and 3 are useful for describing the electro-polishing process using the electro-polishing fixture 10 of the present invention. First, the stent 18 is placed within the holding anodes 12. The stent 18 is centered about the midpoint of each slot 44, thereby ensuring that the exposed section 46 of each anode 12 is in electrical contact along the entire length of the stent. By equally spacing the anodes 12 around the perimeter of the stent, a high degree of uniformity in the electric field density between the stent and the center cathode 14 and the curved exterior cathode 16 is obtained with a consequent uniformity in the polishing of the stent. The polishing fixture 10, with a stent loaded thereon is subsequently placed within a container 30 filled with an electrolyte solution 32. The anodes 12 are electrically connected to a positive terminal 26 of a power supply 20. The cathodes 14 and 16 are subsequently electrically connected to a negative terminal 24 of the power supply 20, thereby forming a complete electric circuit. When electric current is applied to the circuit, atoms of material from the stent and the exposed sections 46 of the anodes 12 are ionized and migrate to the cathodes 14 and 16. Since protrusions ionize faster than depressions, a polishing effect occurs. Because a section of the stent is in contact with an exposed section 46 of each anode 12, these sections are effectively masked from exposure to the electrolyte solution and are not initially polished. Therefore, to ensure polishing of the masked sections, it is necessary to rotate the stent within the holding anodes 12 during the polishing procedure. Polishing cycle time is dependant on the electrolyte used, the size of the stent, and field density between the stent and the cathodes. Field density itself is dependant on the amount of current that can be passed through the anodes, the stent, and the cathodes. Current flow in turn is a function of the resistivity of the anode, stent, and cathode materials and of the applied voltage to the circuit.

Many electrolyte formulations are used in electro-polishing. Most prior art formulations are directed to the polishing of stainless steel. These electrolytes typically contain about 50 to 75% by weight acids, about 5 to 15% by weight deionized water, and the remainder by weight one or more inhibitors. The acid component of the electrolyte commonly consists of phosphoric acid and sulfuric acid mixed in a 1:1 or 2:1 ratio. While the prior art electrolyte solutions are effective in polishing stainless steel, they are relatively ineffective when used with nickel-titanium materials. Modified electrolyte solutions are required in order to achieve the desired surface finish of 0.2 to 0.05 microns surface roughness on nickel-titanium alloys.

A desired surface finish can be obtained on nickel-titanium parts with an electrolyte comprising about 70% to 95% by weight absolution methanol, about 5% to 15% by weight sulfuric acid, and about 1.0% to 6% by weight saturated hydrochloric acid. The presently preferred composition for the electrolyte which forms part of the present invention is a solution comprising 90% by weight absolution methanol, 7% by weight sulfuric acid, and 3% by weight hydrochloric acid.

EXAMPLE

With reference to FIG. 3, the following is a detailed example of polishing a nickel-titanium stent using the electro-polishing fixture and electrolyte of the present invention. A nickel-titanium stent of 8 mm diameter, with a length of 20 mm, with a wall thickness of 0.15 mm and a resistance of 9 ohms was descaled by bead blasting and then placed over the center cathode 14 and within the holding anodes 12 of the polishing fixture 10 of the present invention. Four anodes 12 proved sufficient to maintain a uniform current density between the stent and the cathodes 14 and 16. In order to provide a preferred path for current flow, the anodes 12 possessed a resistence of 0.006 ohms. In order to achieve the desired degree of polishing on the outside of the stent, the curved exterior cathode 16 was radially spaced at 6 mm from the stent exterior surface. The electro-polishing was conducted in about 500 ml of electrolyte 32 which comprised a solution of about 465 ml of absolution methanol, about 37.5 ml of sulfuric acid at a purity of greater than 96.5%, and about 12.5 ml of saturated hydrochloric acid. A current density of about 75 amperes/inch squared at 0.6 volts was applied between the stent and the cathodes. The stent was polished for about 15–80 seconds. To achieve uniform polishing of all portions of the stent, the stent was rotated 5–20 times during the polishing process. Prior to polishing, the stent had a surface roughness of about 5–75 microns. After polishing the stent had a surface roughness of about 0.05–0.2 microns which corresponds to a mirror finish and is suitable for implantation within living tissue.

While the electro-polishing fixture 10 has been described with particular reference to polishing nickel-titanium stents, the polishing fixture is equally applicable with minimal modification to polishing stents made of other metallic materials, such as stainless steel.

As will be understood by one skilled in the art many variations of the embodiments described herein are possible. While the apparatus and method of the invention has been described in terms of the initial developmental embodiments it is understood that the invention as outlined above may be practiced with modifications within the spirit and scope of the claims.

What is claimed is:

1. An electro-polishing fixture for polishing a stent, comprising:

a plurality of anodes adapted to be spaced around the perimeter of the stent to be polished, the anodes being arranged for electrical contact with the stent;

a curved exterior cathode adapted to be disposed in a fixed spatial relationship about the exterior of the stent; and an electrically non-conductive frame arranged for holding the anodes in contact with the stent and for maintaining the curved exterior cathode disposed about the exterior of the stent.

2. The electro-polishing fixture of claim 1 further comprising, a center cathode adapted to extend through the inside of the stent.

3. The electro-polishing fixture of claim 2 wherein, the anodes are adapted to be equally spaced about the perimeter of the stent.

4. The electro-polishing fixture of claim 1 wherein, the anodes are parallel to each other and are arranged to be substantially parallel to the longitudinal axis of the stent.

5. The electro-polishing fixture of claim 1 wherein, the anodes are made from a metal selected from the group consisting of nickel-titanium alloys, platinum, and platinum-iridium alloys.

6. The electro-polishing fixture of claim 5 wherein, the sheath is made of a material selected from the group consisting of polytetrafluoroethylene (PTFE) and fluorinated ethylenepropylene copolymer (FEP).

7. The electro-polishing fixture of claim 1 wherein, the anodes further include a sheath of non-conductive, electro lyte resistant material, a portion of the sheath material being removed to provide electrical contact between the anodes and the stent.

8. The electro-polishing fixture of claim 1 wherein, the center cathode is adapted to be essentially coincident with the longitudinal axis of the stent.

9. The electro-polishing fixture of claim 1 wherein, the center cathode is made of a metal selected from the group consisting of nickel-titanium alloys, platinum, and platinum-iridium alloys.

10. The electro-polishing fixture of claim 9 wherein, the exterior cathode includes a longitudinal axis of symmetry which is arranged to be substantially parallel to the longitudinal axis of the stent to be polished.

11. The electro-polishing fixture of claim 1 wherein, the exterior cathode is adapted to be substantially concentric with the stent to be polished.

12. The electro-polishing fixture of claim 1 wherein, the exterior cathode has an arc length of at least 45 degrees.

13. The electro-polishing fixture of claim 1 wherein, the exterior cathode has an arc length of about 180 degrees.

14. The electro-polishing fixture of claim 1 wherein, the exterior cathode has an arc length of about 360 degrees.

15. The electro-polishing fixture of claim 1 wherein, the exterior cathode is made of a metal selected from the group consisting of nickel-titanium alloys, platinum, and platinum-iridium alloys.

16. An electrolyte solution for polishing stents made from a nickel-titanium alloy comprising:
   about 70% to 90% by weight absolution methanol;
   about 5% to 15% by weight sulfuric acid; and
   about 1% to 6% by weight hydrochloric acid.

17. The electrolyte solution of claim 15 wherein, the absolution methanol is 90% by weight.

18. The electrolyte solution of claim 15 wherein, the sulfuric acid is 7% by weight.

19. The electrolyte solution of claim 15 wherein, the hydrochloric acid is 3% by weight.

20. A method for electro-polishing stents comprising:
   providing a stent to be polished;
   placing the stent in an electro-polishing fixture which includes a center cathode, a curved exterior cathode, and a plurality of anodes;
   immersing the stent containing electro-polishing fixture in an electrolytic bath comprising about 70% to 95% by weight absolution methanol, about 5% to 15% by weight sulfuric acid, and about 1% to 6% by weight hydrochloric acid;
   subjecting the immersed stent to anodic electrolytic treatment at a current density of about 50 to 150 amperes/inch squared at about 0.25 to 1.0 volts between the stent and the cathodes, for a sufficient period of time such that the interior and exterior surfaces of the stent have a surface roughness of no more than 0.5 microns; and
   rotating the stent within the electro-polishing fixture such that all surfaces of the stent are uniformly polished.

* * * * *

UNITED STATES PATENT AND TRADEMARK OFFICE
CERTIFICATE OF CORRECTION

PATENT NO. : 6,375,826 B1
DATED : April 23, 2002
INVENTOR(S) : Jingli Wang et al.

It is certified that error appears in the above-identified patent and that said Letters Patent is hereby corrected as shown below:

<u>Title page,</u>
Item [56], References Cited, FOREIGN PATENT DOCUMENTS, change "WO 2001/06954", to read -- WO 01/06954 --.

Signed and Sealed this

Tenth Day of September, 2002

Attest:

JAMES E. ROGAN
*Attesting Officer*     *Director of the United States Patent and Trademark Office*